(12) United States Patent
Cantat et al.

(10) Patent No.: US 9,663,452 B2
(45) Date of Patent: May 30, 2017

(54) METHOD FOR PREPARING FORMAMIDINES

(71) Applicant: Commissariat A L'Energie Atomique Et Aux Energies Alternatives, Paris (FR)

(72) Inventors: Thibault Cantat, Issy les Moulineaux (FR); Jacky Pouessel, Massy (FR); Olivier Jacquet, Orsay (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/433,985

(22) PCT Filed: Oct. 11, 2013

(86) PCT No.: PCT/IB2013/059304
§ 371 (c)(1),
(2) Date: Apr. 7, 2015

(87) PCT Pub. No.: WO2014/057466
PCT Pub. Date: Apr. 17, 2014

(65) Prior Publication Data
US 2015/0266813 A1 Sep. 24, 2015

(30) Foreign Application Priority Data

Oct. 12, 2012 (FR) .................................... 12 59757

(51) Int. Cl.
| | | |
|---|---|---|
| *C07C 275/28* | (2006.01) |
| *C07C 275/04* | (2006.01) |
| *C07C 249/02* | (2006.01) |
| *C07C 257/12* | (2006.01) |
| *A01N 37/52* | (2006.01) |
| *A01N 43/50* | (2006.01) |
| *A61K 31/155* | (2006.01) |
| *A61K 31/4164* | (2006.01) |
| *C07D 233/64* | (2006.01) |

(52) U.S. Cl.
CPC ............ *C07C 249/02* (2013.01); *A01N 37/52* (2013.01); *A01N 43/50* (2013.01); *A61K 31/155* (2013.01); *A61K 31/4164* (2013.01); *C07C 257/12* (2013.01); *C07D 233/64* (2013.01)

(58) Field of Classification Search
CPC ... C07C 275/28; C07C 249/02; C07C 275/04; A61K 31/155; A01N 37/52
USPC ......................................... 564/225, 245, 48
See application file for complete search history.

(56) References Cited

PUBLICATIONS

International Search Report and Written Opinion for Application No. PCT/IB2013/059304 dated Feb. 27, 2014.
Kikugawa, Y. et al., *The Reaction of Substituted Ureas With Sodium Borohydride in Pyridine*, Tetrahedron Letters, vol. 10, No. 9 (Jan. 1969) 699-702 (XP055069547).
Larizza, A. et al., *The Reaction of Substituted Ureas With Lithium Aluminum Hydride. I. A New Synthesis of Three-Substitute Formamidines*, The Journal of Organic Chemistry, vol. 29, No. 12 (Dec. 1964) 3697-3700 (XP055069551).
Torizuka, M. et al., *Synthesis of Hexasubstituted Carbamimidic Acid Anhydrides and an $N^1$, $N^1$, $N^2$-Trisubstituted Formamidines From 1,1,3-TrisubstitutedUreas*, Synthesis, vol. 1986, No. 3 (Jan. 1986) pp. 226-228 (XP055069545).

*Primary Examiner* — Alicia L Otton
*Assistant Examiner* — Sagar Patel
(74) *Attorney, Agent, or Firm* — Alston & Bird LLP

(57) ABSTRACT

A method for preparing formamidines of formula (I) in a single step by reducing ureas of formula (II) using silanes of formula (III), according to reaction (II)+(III)+(I) is provided. The present invention also provides a method for preparing insecticides, pesticides, fungicides, pharmaceutical products and catalysts, including a step of preparing formamidines of formula (I) according to the invention.

19 Claims, No Drawings

METHOD FOR PREPARING FORMAMIDINES

FIELD

The present invention relates to a process for the preparation, in a single stage, of formamidines by catalytic hydrosilylation of organic ureas.

BACKGROUND

Formamidines are basic molecules in the chemical industry. They are used in various industries and in particular for their applications as:
- insecticides, pesticides, fungicides (J. Agric. Food Chem., 1977, Vol. 25, No. 3, 493-501; Ecotoxicology and Environmental Safety, 1996, 33, 163-167; J. Agric. Food Chem., 1969, Vol. 17, No. 3, 595-600; Bull. Environ. Contam. Toxicol., 2000, 65, 22-27),
- pharmaceutical active principles (Clin. Pharmacol. Ther., 1999, 65, 369-376; Eur. J. Pharmacol., 1994, 288, 17-25),
- synthesis reactants (Chem. Rev., 2011, 111, 2705-2733; Org. Lett., 2009, Vol. 11, No. 4, 1019-1022),
- ligand for the preparation of catalysts (Eur. J. Org. Chem., 2010, 4893-4901).

Thus, the present invention also relates to a process for the manufacture of insecticides, pesticides, fungicides, pharmaceutical products and catalysts comprising a stage of preparation of formamidines according to the process of the invention. Formamidines can also be used as intermediates in the synthesis of N-heterocyclic carbenes (Chem. Rev., 2011, 111, 2705-2733; Org. Lett., 2009, Vol. 11, No. 4, 1019-1022), or in the synthesis of alkaloids used in therapeutic chemistry (J. Org. Chem., 1996, 61, 573-580).

The synthesis of formamidines by reduction of organic ureas (also known as ureas) is an attractive synthesis route as ureas are stable and relatively nontoxic compounds which can be prepared in a simple way from carbon dioxide $CO_2$ (Angew. Chem. Int. Ed., 2003, 42, 3257-3260; Green Chem., 2010, 12, 1811-1816).

However, the carbonyl functional groups of ureas are very difficult to reduce due to their thermodynamic stability (Angew. Chem. Int. Ed., 2011, 50, 11702-11705). Their reduction requires the use of powerful reducing agents, such as lithium aluminum hydride ($LiAlH_4$) (J. Org. Chem., 1964, 29, 3697-3700; J. Org. Chem., 1950, 15, 1020-1022) or sodium borohydride ($NaBH_4$) (Tetrahedron Lett., 1969, No. 9, 699-702), which exhibit the disadvantage of also reducing other functional groups which may be present.

The use of mild reducing agents, such as hydrogen, has ended in failure. This is because the urea is directly reduced to amines and methanol and the formamidine compound as such cannot be isolated (Angew. Chem. Int. Ed., 2011, 50, 11702-11705).

The inventors have discovered that the silanes corresponding to the following formula (III):

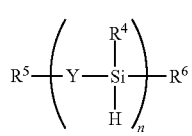

(III)

are attractive reducing agents for the reduction of ureas to give formamidines insofar as they are not very reactive, tolerated by functional groups (other than the carbonyl functional groups of the ureas), available commercially, stable and not very toxic (J. Chem. Soc., Perkin Trans. 1, 1999, 3381-3391).

Thus, the present invention relates to a process for the synthesis of formamidines of formula (I) by reduction of ureas of formula (II) by silanes of formula (In), according to the following reaction:

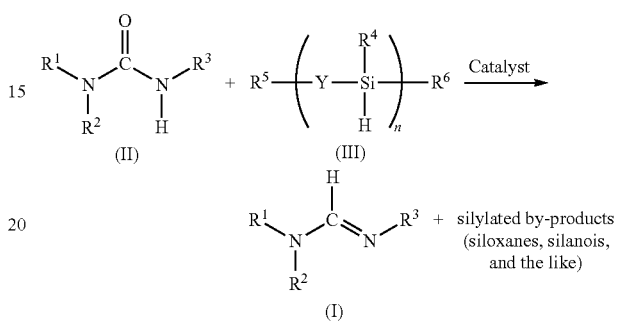

Conventionally, formamidines of general formula (I) are synthesized by condensation of a formamide of formula $R^1R^2NCOH$ with an amine of formula $R^3NH_2$ in the presence of a strong dehydrating agent, such as thionyl chloride ($SOCl_2$) (J. Med. Chem., 1988, 31, 1816-1820), phosphoryl trichloride ($POCl_3$) (Eur. J. Org. Chem., 2010, 4893-4901; Bioorg. Med. Chem. Lett., 2010, 20, 6781-6784) or trifluoroacetic anhydride (Tetrahedron, 2006, 62, 5617-5625). These synthesis routes generally require moderate to strong heating which can range up to 180° C. and involve the handling of toxic reactants ($SOCl_2$, $POCl_3$, and the like).

An alternative route consists of the synthesis of formamidines by reaction between a primary amine and a trialkyl orthoformate, for example $(EtO)_3CH$ or $(MeO)_3CH$ (Org. Lett., 2009, Vol. 11, No. 4, 1019-1022; Synlett., 2011, No. 3, 405-409; J. Am. Chem. Soc., 1954, 76, 3978-3982).

Formamidines can also be obtained by reduction of the corresponding ureas. This method may appear attractive insofar as ureas can be easily prepared by condensation of amines with carbon dioxide $CO_2$, which are molecules which are stable and easy to store. The synthesis of formamidines then requires the use of powerful reducing agents, such as $LiAlH_4$, $NaBH_4$, triethyl orthoformate ($(EtO)_3CH$) (J. Am. Chem. Soc., 1955, 77, 5872-5877) or a dimethylaminoborane/trichlorophosphate mixture (Synthesis-Stuttgart, 1986, No. 3, 226-228).

The methods described in the state of the art thus require the use of reactants which are toxic ($POCl_3$) or unstable with regard to water ($LiAlH_4$, $NaBH_4$, $(EtO)_3CH$) and consequently difficult to store. Furthermore, they are not very selective and are incompatible with the presence of functional groups.

There thus exists a real need for a process for the preparation of formamidines which overcomes the disadvantages of the prior art and which makes it possible to obtain, in a single stage with a good yield and an excellent selectivity, formamidines by reduction of ureas by silanes, while not reducing the other functional groups which may be present on the urea.

SUMMARY

The inventors have succeeded in developing a process for the synthesis of formamidines in a single stage via a unique reaction unknown to date.

The synthesis process for the present invention combines the following advantages over the existing systems:
the use of organic ureas as starting material, and
the use of hydrosilanes as reducing agents, the latter being known to be stable, not very toxic and tolerated by numerous functional groups.

Thus, a first subject matter of the invention is a process for the preparation of formamidines of formula (I):

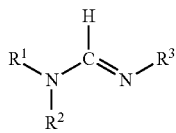
(I)

in which:
$R^1$, $R^2$ and $R^3$ represent, independently of one another, a hydrogen atom, an alkyl, alkenyl, alkynyl, aryl or heteroaryl group, a heterocycle or a silyl, siloxy or amino group, said alkyl, alkenyl, alkynyl, aryl, heteroaryl, heterocycle, silyl, siloxy and amino groups optionally being substituted, or
$R^1$ and $R^2$, taken together with the nitrogen atom to which they are bonded, form an optionally substituted heterocycle, or
$R^1$ and $R^3$, taken together with the nitrogen atom to which they are bonded, form an optionally substituted heterocycle,
characterized in that a urea of formula (II), in which $R^1$, $R^2$ and $R^3$ are as defined above:

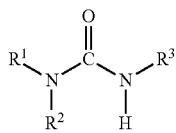
(II)

is reacted, in the presence of a catalyst, with a silane compound of formula (III):

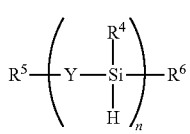
(III)

in which n is an integer varying from 1 to 20 000, and
when n=1 and Y represents a single bond, and
$R^4$, $R^5$ and $R^6$ represent, independently of one another, a hydrogen or halogen atom, a hydroxyl, alkyl, alkenyl, alkynyl, aryl or alkoxy group or a silyl, siloxy or amino group, said alkyl, alkenyl, alkynyl, aryl, alkoxy, silyl, siloxy and amino groups optionally being substituted, or
$R^6$ is as defined above and $R^4$ and $R^5$, taken together with the silicon atom to which they are bonded, form an optionally substituted silylated heterocycle, or
when n>1, Y is an oxygen atom, and
$R^4$ represents a hydrogen or a halogen atom or an alkyl or alkoxy group,
$R^5$ represents a silyl group of formula —Si(X)$_3$ in which each X group, independently of one another, is chosen from a hydrogen or halogen atom or an alkyl or alkoxy group,
$R^6$ represents a siloxy group of formula —O—Si(X)$_3$ in which each X group, independently of one another, is chosen from a hydrogen or halogen atom, or an alkyl or alkoxy group.

DETAILED DESCRIPTION

The process of the invention has the advantage of making possible the synthesis of formamidines with a good yield (of the order of 30% to 100%) and a very good selectivity.

In the context of the present invention, the yield is calculated with respect to the amount of urea of formula (II) initially introduced, on the basis of the amount of formamidine of formula (I) isolated:

Yield=$n$(urea)/($n$(urea)+$n$(formamidine)), n being the amount of material.

In the context of the present invention, the selectivity refers to the nature of the products formed from the urea of formula (II).

Within the meaning of the present invention, "alkyl" is understood to mean an optionally substituted, linear, branched or cyclic and saturated or unsaturated carbon-based radical comprising from 1 to 12 carbon atoms. Mention may be made, as saturated and linear or branched alkyl, for example, of the methyl, ethyl, propyl, butyl, pentyl, hexyl, heptyl, octyl, nonyl, decyl, undecyl and dodecanyl radicals and their branched isomers. Mention may be made, as cyclic alkyl, of the cyclopropyl, cyclobutyl, cyclopentyl, cyclohexyl, bicyclo[2.1.1]hexyl and bicyclo[2.2.1]heptyl radicals. Mention may be made, as unsaturated cyclic alkyls, for example, of cyclopentenyl and cyclohexenyl. The unsaturated alkyls also known as "alkenyl" or "alkynyl" respectively comprise at least one double or one triple bond. Mention may be made, as such, for example, of the ethylenyl, propylenyl, butenyl, pentenyl, hexenyl, acetylenyl, propynyl, butynyl, pentynyl and hexynyl radicals and their branched isomers. The alkyl group, within the meaning of the invention including the alkenyl and alkynyl groups, can optionally be substituted by one or more hydroxyl groups, one or more alkoxy groups, one or more halogen atoms chosen from fluorine, chlorine, bromine and iodine atoms, one or more nitro (—NO$_2$) groups, one or more nitrile (—CN) groups, or one or more aryl groups, with the alkoxy and aryl groups as defined in the context of the present invention.

The term "aryl" denotes generally a cyclic aromatic substituent comprising from 6 to 20 carbon atoms. In the context of the invention, the aryl group can be mono- or polycyclic. Mention may be made, by way of indication, of the phenyl, benzyl and naphthyl groups. The aryl group can optionally be substituted by one or more hydroxyl groups, one or more alkoxy groups, one or more halogen atoms chosen from fluorine, chlorine, bromine and iodine atoms, one or more nitro (—NO$_2$) groups, one or more nitrile (—CN) groups, one or more alkyl groups or one or more aryl groups, with the alkoxy, alkyl and aryl groups as defined in the context of the present invention.

The term "heteroaryl" denotes generally a mono- or polycyclic aromatic substituent comprising from 5 to 10 members, including at least 2 carbon atoms and at least one heteroatom chosen from nitrogen, oxygen or sulfur. The heteroaryl group can be mono- or polycyclic. Mention may be made, by way of indication, of the furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, pyrazolyl, oxazolyl, isoxazolyl, benzoxazolyl, thiazolyl, benzothiazolyl, isothiazolyl, pyridazinyl, pyrimidilyl, pyrazinyl, triazinyl, cinnolinyl, phthalazinyl and quinazolinyl groups. The heteroaryl group can optionally be substituted by one or more hydroxyl groups, one or more alkoxy groups, one or more halogen atoms chosen from fluorine, chlorine, bromine and iodine atoms, one or more nitro (—$NO_2$) groups, one or more nitrile (—CN) groups, one or more aryl groups or one or more alkyl groups, with the alkyl, alkoxy and aryl groups as defined in the context of the present invention.

The term "alkoxy" means an alkyl group, as defined above, bonded via an oxygen atom (—O-alkyl).

The term "heterocycle" denotes a saturated or unsaturated and mono- or polycyclic substituent comprising from 5 to 10 members and comprising from 1 to 4 heteroatoms chosen, independently of one another, from nitrogen, oxygen and sulfur. Mention may be made, by way of indication, of the morpholinyl, piperidinyl, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl and isothiazolidinyl substituents. The heterocycle can optionally be substituted by one or more hydroxyl groups, one or more alkoxy groups, one or more aryl groups, one or more halogen atoms chosen from fluorine, chlorine, bromine and iodine atoms, one or more nitro (—$NO_2$) groups, one or more nitrile (—CN) groups or one or more alkyl groups, with the alkyl, alkoxy and aryl groups as defined in the context of the present invention.

Halogen atom is understood to mean an atom chosen from fluorine, chlorine, bromine or iodine atoms.

"Silyl" group is understood to mean a group of formula —$Si(X)_3$ in which each X group, independently of one another, is chosen from a hydrogen atom, one or more halogen atoms chosen from fluorine, chlorine, bromine or iodine atoms, one or more alkyl groups, one or more aryl groups or one or more alkoxy groups, with the alkyl, aryl and alkoxy groups as defined in the context of the present invention.

"Siloxy" group is understood to mean a silyl group, as defined above, bonded via an oxygen atom (—O—$Si(X)_3$).

Within the meaning of the invention, "silylated heterocycle" is understood to mean a saturated or unsaturated and mono- or polycyclic substituent comprising from 5 to 15 members and comprising at least one silicon atom and optionally at least one other heteroatom chosen from nitrogen, oxygen or sulfur. Said silylated heterocycle can optionally be substituted by one or more hydroxyl groups, one or more alkyl groups, one or more alkoxy groups, one or more halogen atoms chosen from fluorine, chlorine, bromine and iodine atoms or one or more aryl groups, with the alkyl, alkoxy and aryl groups as defined in the context of the present invention. Mention may be made, among silylated heterocycles, for example, of 1-silacyclo-3-pentene or 1-methyl-1-hydrido-2,3,4,5-tetraphenyl-1-silacyclopentadiene, corresponding to the formulae below:

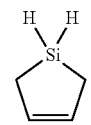 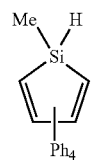

1-silacyclo-3-pentene    1-methyl-1-hydrido-2,3,4,5-tetraphenyl-1-silacyclopentadiene Mention may also be made, for example, of methylsiloxane, 1-phenyl-1-silacyclohexane, 1-silabicyclo[2.2.1]heptane, 1-methyl-1-silacyclopentane and 9,9-dihydro-9-silafluorene, corresponding to the formulae below:

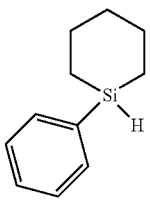 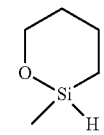 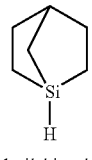

1-phenyl-1-silacyclohexane    methylsiloxane    1-silabicyclo[2.2.1]heptane

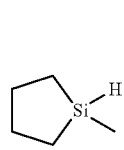 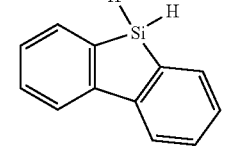

1-methyl-1-silacyclopentane    9,9-dihydro-9-silafluorene

The silylated heterocycles of the invention can be available commercially or can, if appropriate, be prepared by known synthesis processes, such as, for example, those described by C. L. Smith et al., J. Org. Chem., 1974, 81, 33-40; G. D. Homer, J. Am. Chem. Soc., 1973, 95:23, 7700-7707; L. Spialter et al., J. Am. Chem. Soc., 1971, 93:22, 5682-5686; R. West, J. Am. Chem. Soc., 1954, 76, 6015-6017. A person skilled in the art is in a position to employ and adapt the known processes to the synthesis of the various silylated heterocycles which he needs.

"Amino" group is understood to mean a group of formula —$NR^7R^8$ in which:
  $R^7$ and $R^8$ represent, independently of one another, a hydrogen atom, an alkyl, alkenyl, alkynyl, aryl or heteroaryl group, a heterocycle or a silyl or siloxy group, with the alkyl, alkenyl, alkynyl, aryl, heteroaryl, heterocycle, silyl and siloxy groups as defined in the context of the present invention; or
  $R^7$ and $R^8$, taken together with the nitrogen atom to which they are bonded, form a heterocycle optionally substituted by one or more hydroxyl groups, one or more alkyl groups, one or more alkoxy groups, one or more halogen atoms chosen from fluorine, chlorine, bromine and iodine atoms, one or more nitro (—$NO_2$) groups, one or more nitrile (—CN) groups or one or more aryl groups, with the alkyl, alkoxy and aryl groups as defined in the context of the present invention.

According to an alternative form of the invention, the $R^1$, $R^2$ and $R^3$ groups of the urea of formula (II) represent, independently of one another, a hydrogen atom, a linear or branched $C_1$-$C_7$ alkyl group, a $C_5$-$C_6$ heterocycle, an aryl group chosen from phenyl or benzyl or a heteroaryl group chosen from imidazolyl or benzimidazolyl, said alkyl, heterocyclic, aryl or heteroaryl groups optionally being substituted by one or more hydroxyl groups, one or more alkyl groups, one or more alkoxy groups, one or more halogen atoms chosen from fluorine, chlorine, bromine and iodine atoms, one or more nitro (—$NO_2$) groups, one or more nitrile (—CN) groups or one or more aryl groups, with the alkyl, alkoxy and aryl groups as defined in the context of the present invention.

According to a preferred embodiment of the invention, in the silane compound of formula (III):
  n=1 and Y represents a single bond, and
  $R^4$, $R^5$ and $R^6$ represent, independently of one another, a hydrogen atom, an alkyl, aryl or alkoxy group or a silyl or siloxy group, said alkyl, aryl, alkoxy, silyl and siloxy groups optionally being substituted, and, preferably, $R^4$, $R^5$ and $R^6$ represent, independently of one another:
    a hydrogen atom,
    a linear or branched $C_1$-$C_7$ alkyl group,
    an aryl group chosen from phenyl or benzyl,
    a linear or branched $C_1$-$C_7$ alkoxy group,
    a silyl group of formula —Si(X)$_3$ in which each X group, independently of one another, is chosen from a hydrogen or halogen atom, or an alkyl or alkoxy group,
    a siloxy group of formula —O—Si(X)$_3$ in which each X group, independently of one another, is chosen from a hydrogen or halogen atom, or an alkyl or alkoxy group.

Preferably, when the silane compound of formula (III) is a silane compound in which n=1, it is chosen, for example, from PhSiH$_3$, Ph$_2$SiH$_2$, (EtO)$_3$SiH or (CH$_3$)$_2$HSiOSiH(CH$_3$)$_2$.

According to another preferred embodiment of the invention, in the silane compound of formula (III):
  n>1, advantageously n varies from 1000 to 5000, and Y is an oxygen atom, and
  $R^4$ is chosen from a hydrogen atom or a methyl group,
  $R^5$ represents a silyl group of formula —Si(X)$_3$ in which each X group, independently of one another, is chosen from a hydrogen or halogen atom, or an alkyl or alkoxy group,
  $R^6$ represents a siloxy group of formula —O—Si(X)$_3$ in which each X group, independently of one another, is chosen from a hydrogen or halogen atom, or an alkyl or alkoxy group.

Preferably, when the silane compound of formula (III) is a polymeric organosilane (n>1), the latter can, for example, be polymethylhydrosiloxane (PMHS).

When the silane compound of formula (III) is a polymeric organosilane, the number of equivalents introduced into the reaction medium is given with respect to the number of hydrides introduced and consequently to the number of monomers introduced, with respect to the urea of formula (II).

Catalyst, within the meaning of the invention, is understood to mean any compound which is capable of modifying, in particular by increasing, the rate of the chemical reaction in which it participates and which is regenerated at the end of the reaction. This definition encompasses both catalysts, that is to say compounds which exert their catalytic activity without having to be subjected to any modification or conversion, and compounds (also known as precatalysts) which are introduced into the reaction medium and which are converted therein into a catalyst.

The catalysts can be chosen from organic catalysts or metal catalysts, the metal catalysts being chosen from metal salts or metal complexes. Organic catalysts exhibit the advantage of making it possible to escape the problems of toxicity generally observed for metal catalysts and also the problems of costs associated with the use of precious metals. In the process of the invention, the catalyst is preferably a metal salt used in the presence or absence of a ligand.

The organic catalysts are generally organic bases chosen from:
  nitrogenous bases, such as, for example, secondary or tertiary amines chosen from triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt or N-diisopropylethylamine (DIPEA or DIEA); or
  phosphorus-based bases, such as, for example, alkyl- and arylphosphines chosen from triphenylphosphine, 2,2'-bis(diphenylphosphino)-1,1'-binaphthyl (BINAP) or triisopropylphosphine; alkyl- and arylphosphonates chosen from diphenyl phosphate, triphenyl phosphate (TPP), tri(isopropylphenyl)phosphate (TIPP), cresyl diphenyl phosphate (CDP) or tricresyl phosphate (TCP); or alkyl and aryl phosphates chosen from di(n-butyl)phosphate (DBP), tris(2-ethylhexyl)phosphate or triethyl phosphate;
  carbon-based bases for which the protonation takes place on a carbon atom, such as, for example, an N-heterocyclic carbene, such as a carbene resulting from an imidazolium salt chosen from 1,3-bis(2,6-diisopropylphenyl)-1H-imidazol-3-ium, 1,3-bis(2,6-diisopropylphenyl)-4,5-dihydro-1H-imidazol-3-ium, 1,3-bis(2,4,6-trimethylphenyl)-1H-imidazol-3-ium, 1,3-bis(2,4,6-trimethylphenyl)-4,5-dihydro-1H-imidazol-3-ium, 4,5-dichloro-1,3-bis(2,6-diisopropylphenyl)-1H-imidazol-3-ium, 1,3-di(tert-butyl)-1H-imidazol-3-ium or 1,3-di(tert-butyl)-4,5-dihydro-1H-imidazol-3-ium salts, said salts being, for example, in the form of chloride salts, as represented below:

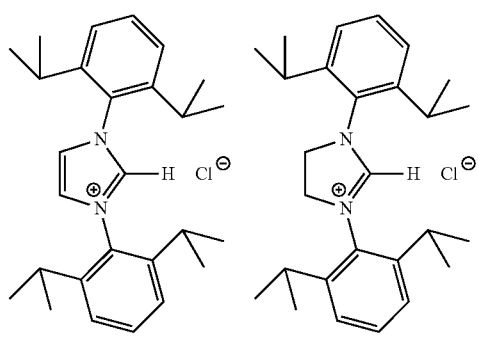

-continued or
oxygen-based bases, such as, for example, hydrogen peroxide, benzoyl peroxide or an alkoxide chosen from sodium or potassium methoxide, ethoxide, propoxide, butoxide, pentoxide or hexoxide.

According to a preferred alternative form of the invention, the organic catalyst is chosen from triazabicyclodecene (TBD), N-methyltriazabicyclodecene (MeTBD) or 1,8-diazabicyclo[5.4.0]undec-7-ene (DBU).

When the catalyst is a metal catalyst, it can be chosen from the salts or complexes of:
  metals chosen from boron, silicon, aluminum, gallium, tin or indium;
  alkali metals chosen from sodium and potassium;
  alkaline earth metals chosen from magnesium and calcium;
  transition metals chosen from nickel, iron, cobalt, zinc, copper, rhodium, ruthenium, platinum, palladium or iridium;
  rare earth metals chosen from lanthanum, cerium, praseodymium or neodymium.

Preferably, the metal catalyst is a salt or complex of a transition metal chosen from nickel, iron, cobalt, zinc, copper, rhodium, ruthenium, platinum, palladium or iridium, or more preferably still from iron, zinc, copper or ruthenium.

By way of examples, the metal catalyst can be chosen from the following salts or complexes:

Al(OiPr)$_3$, SnCl$_2$ or InBr$_3$, as metal salts or complexes;
Na$_2$CO$_3$, K$_2$CO$_3$ or Cs$_2$CO$_3$, as salts or complexes of alkali metals;
MgSO$_4$ or Ca(BH$_4$)$_2$, as salts or complexes of alkaline earth metals;
Fe(BH$_4$)$_2$.6H$_2$O, Fe(BF$_4$)$_2$.6H$_2$O, Fe(acac)$_3$, CuCl, Cu(OAc)$_2$(H$_2$O), Zn(OAc)$_2$, Zn(BDI)Et or ZnEt$_2$, as salts or complexes of transition metals;
La(OTf)$_3$ or CeCl$_3$, as salts or complexes of rare earth metals.

Metal complex is understood to mean an organometallic or inorganic coordination compound in which a metal ion is bonded to an organic or inorganic ligand. An organometallic or inorganic complex can be obtained by mixing a metal salt with a ligand, the latter bonding to the metal via phosphorus, carbon, nitrogen, oxygen, hydrogen or silicon atoms, for example. Mention may be made, as organic or inorganic ligand, by way of indication, of a ligand of the phosphine or amine type, such as, for example, tris[2-(diphenylphosphino)ethyl]phosphine (PP$_3$), tricyclohexylphosphine, acetate (AcO), acetylacetonate (acac), 1,2-bis(diphenylphosphino)ethane (dppe), N,N,N',N'-tetramethylethylenediamine (TMEDA), N,N'-bis(2,6-diisopropylphenyl)-β-diketiminate (BDI), 1,2-bis(diphenylphosphino)benzene (dppb) or pyridine.

According to a preferred alternative form of the invention, the metal catalyst is:
  a mixture of an iron metal salt, such as, for example, Fe(acac)$_3$, Fe(acac)$_2$ or Fe(BF$_4$)$_2$.6H$_2$O, with a ligand of phosphine or amine type, such as, for example TMEDA, dppe or PP$_3$; or
  a mixture of a Cu(OAc)$_2$.H$_2$O or Cu(acac)$_2$ copper salt with a ligand of phosphine or amine type chosen from TMEDA, dppe or dpp; or
  a Zn(Et)$_2$ zinc salt; or
  a mixture of an RuCl$_2$(DMSO)$_4$ ruthenium salt with a ligand of phosphine type chosen from PP$_3$ or dpp.

Some of the abbreviations used for the ligands are represented below:

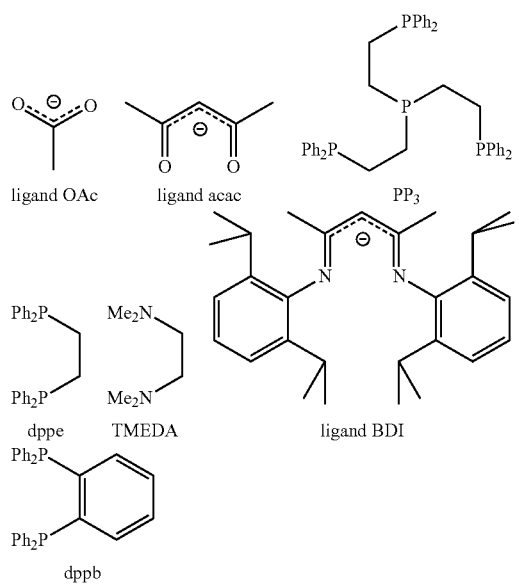

The catalysts can, if appropriate, be immobilized on heterogeneous supports in order to ensure ready separation of said catalyst and/or the recycling thereof. Said heterogeneous supports can be chosen from supports based on silica gel or on plastic polymers, such as, for example, polystyrene, carbon-based supports chosen from carbon nanotubes, silicon carbide, alumina or magnesium chloride ($MgCl_2$).

In the process according to the invention, the reaction temperature can be between 20 and 150° C., and preferably between 75 and 125° C.

The reaction can be carried out for a period of time ranging from 1 to 72 hours, and preferably from 1 to 48 hours.

The process of the invention, in particular the reaction between the different reactants, can take place in one or more solvents chosen from:
 ethers, preferably diethyl ether or THF;
 hydrocarbons, preferably benzene or toluene;
 nitrogenous solvents, preferably pyridine or acetonitrile;
 sulfoxides, preferably dimethyl sulfoxide;
 alkyl halides, preferably chloroform or methylene chloride.

The molar ratio of the urea of formula (II) to the silane compound of formula (III) is from 0.5 to 5, and preferably from 1 to 3.

The amount of catalyst is from 0.001 to 1 molar equivalent, and preferably from 0.001 to 1 molar equivalent, with respect to the urea of formula (II).

The different reactants used in the process of the invention (the ureas of formula (II), the silane compounds of formula (III), the catalysts, and the like) are generally commercial compounds or compounds which can be prepared by any process known to a person skilled in the art.

Another subject matter of the invention is a process for the preparation of insecticides, pesticides, fungicides, pharmaceutical products and catalysts comprising a stage of preparation of formamidines of formula (I) according to the process of the invention.

In addition to the preceding provisions, the invention also comprises other provisions which will emerge from the remainder of the description which follows, which relates to examples of the synthesis of formamidines of formula (I) according to the process of the invention.

EXAMPLES

The hydrosilylation reaction of the ureas of formula (II) to give formamidines of formula (I) is carried out according to the following experimental protocol.

The urea of formula (I) (1 equivalent), the catalyst (from 0.001 to 1 equivalent), the silane (1 to 3 equivalents) and the solvent are introduced, under an inert atmosphere, in a glove box, into a Schlenk tube which is subsequently sealed by a J. Young® tap. The concentration of urea and of silane in the reaction mixture is approximately 0.5 mol·l$^{-1}$ (concentration calculated on the basis of the volume of solvent introduced). The Schlenk tube is subsequently heated at a temperature of 100° C. until the urea has completely converted (reaction for 24 hours). Once the reaction is complete, the mixture is acidified with a 1N aqueous hydrochloric acid solution and the aqueous phase is washed 3 times with ether. Potassium hydroxide pellets are subsequently added to the aqueous phase up to basic pH and then extraction is carried out 3 times with ethyl acetate. After drying the organic phase over anhydrous magnesium sulfate, the ethyl acetate is evaporated under reduced pressure and the pure formamidine is obtained in the form of a white solid. In the event of the presence of other organic by-products, the formamidine can be purified by chromatography on silica gel. The use of a dichloromethane/methanol mixture as eluant makes it possible to obtain the analytically pure formamidine.

The reaction scheme is as follows:

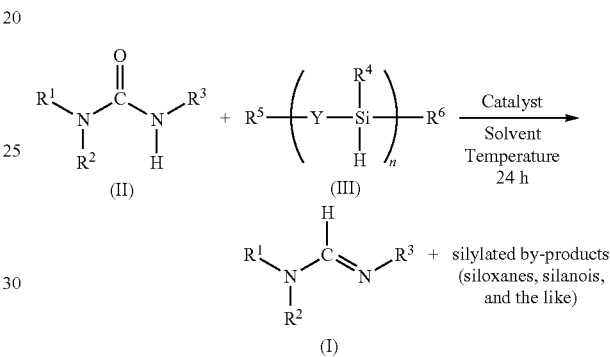

Two different sources of reducing agents were used: phenylsilane and polymethylhydrosiloxane (PMHS). In the case of the PMHS, as the silane is a polymer, the number of equivalents introduced is given with respect to the number of hydrides introduced and thus to the number of monomers introduced, with respect to the urea. Thus, the introduction of 3 equivalents of PMHS corresponds to the introduction of 3 equivalents of hydride and thus 3 equivalents of PMHS monomers, with respect to the urea.

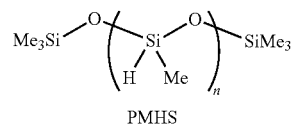

PMHS

Different catalysts were tested for the reaction.
A set of results is presented in the following table 1:

TABLE 1

| Urea of formula (II) | Silane of formula (III) | Catalyst | Solvent | T (° C.) | Yield % |
|---|---|---|---|---|---|
| ![structure] | $PhSiH_3$ (1 eq.) | $Fe(BF_4)·6H_2O$ (5.0 mol %) + $PP_3$ (5.0 mol %) | THF | 100° C. | 91% |

TABLE 1-continued

| Urea of formula (II) | Silane of formula (III) | Catalyst | Solvent | T (° C.) | Yield % |
|---|---|---|---|---|---|
| PhNHC(O)NHPh | PhSiH₃ (1 eq.) | Fe(acac)₂ (5.0 mol %) + PP₃ (5.0 mol %) | THF | 100° C. | 98% |
| PhNHC(O)NHPh | PhSiH₃ (1 eq.) | Fe(acac)₂ (5.0 mol %) + dppb (5.0 mol %) | THF | 100° C. | 34% |
| PhNHC(O)NHPh | PMHS (3 eq.) | Cu(OAc)₂•H₂O (5.0 mol %) + dppb (7.5 mol %) | THF | 100° C. | 30% |
| PhNHC(O)NHPh | Ph₂SiH₂ (1 eq.) | Cu(OAc)₂•H₂O (10.0 mol %) + dppb (15 mol %) | THF | 100° C. | 32% |
| PhNHC(O)NHPh | (EtO)₃SiH (1 eq.) | Cu(OAc)₂•H₂O (10.0 mol %) + dppb (15 mol %) | THF | 100° C. | 83% |
| PhNHC(O)NHPh | TMDS (6 eq.) | Cu(OAc)₂•H₂O (10.0 mol %) + dppb (15 mol %) | THF | 100° C. | 30% |
| PhNHC(O)NHPh | PhSiH₃ (1 eq.) | Zn(Et)₂ (5.0 mol %) | THF | 100° C. | 35% |
| BnNHC(O)NHBn | PhSiH₃ (1 eq.) | Fe(acac)₂ (5.0 mol %) + PP₃ (5.0 mol %) | THF | 100° C. | 39% |
| C₇H₁₅NHC(O)NHC₇H₁₅ | PhSiH₃ (1 eq.) | Fe(acac)₂ (5.0 mol %) + PP₃ (5.0 mol %) | THF | 100° C. | 64% |
| (4-MeOC₆H₄)NHC(O)NH(4-MeOC₆H₄) | PhSiH₃ (1 eq.) | Fe(acac)₂ (5.0 mol %) + PP₃ (5.0 mol %) | THF | 100° C. | 31% |

TABLE 1-continued

| Urea of formula (II) | Silane of formula (III) | Catalyst | Solvent | T (° C.) | Yield % |
|---|---|---|---|---|---|
| 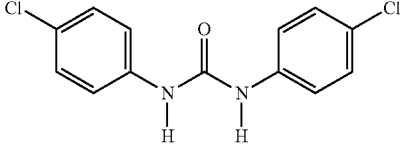 [SMILES: O=C(Nc1ccc(Cl)cc1)Nc1ccc(Cl)cc1] | PhSiH₃ (1 eq.) | Fe(acac)₂ (5.0 mol %) + PP₃ (5.0 mol %) | THF | 100° C. | 81% |
| 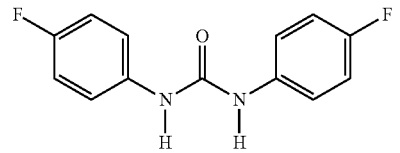 [SMILES: O=C(Nc1ccc(F)cc1)Nc1ccc(F)cc1] | PhSiH₃ (1 eq.) | Fe(acac)₂ (5.0 mol %) + PP₃ (5.0 mol %) | THF | 100° C. | 56% |
| 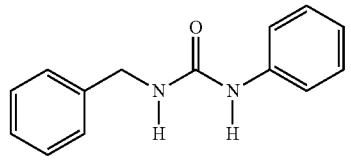 [SMILES: O=C(NCc1ccccc1)Nc1ccccc1] | PhSiH₃ (1 eq.) | Fe(acac)₂ (5.0 mol %) + PP₃ (5.0 mol %) | THF | 100° C. | 61% |
| 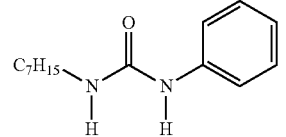 | PhSiH₃ (1 eq.) | Fe(acac)₂ (10.0 mol %) + PP₃ (10.0 mol %) | THF | 100° C. | 65% |
| 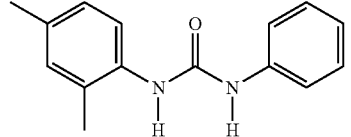 [SMILES: Cc1ccc(NC(=O)Nc2ccccc2)c(C)c1] | PhSiH₃ (1 eq.) | Fe(acac)₂ (5.0 mol %) + PP₃ (5.0 mol %) | THF | 100° C. | 74% |
| 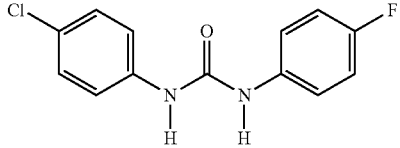 [SMILES: O=C(Nc1ccc(F)cc1)Nc1ccc(Cl)cc1] | PhSiH₃ (1 eq.) | Fe(acac)₂ (5.0 mol %) + PP₃ (5.0 mol %) | THF | 100° C. | 46% |
| 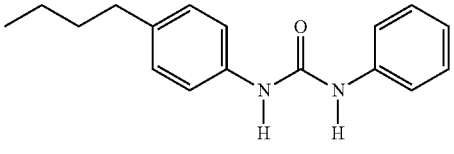 [SMILES: CCCCc1ccc(NC(=O)Nc2ccccc2)cc1] | PhSiH₃ (1 eq.) | Fe(acac)₂ (5.0 mol %) + PP₃ (5.0 mol %) | THF | 100° C. | 46% |
| 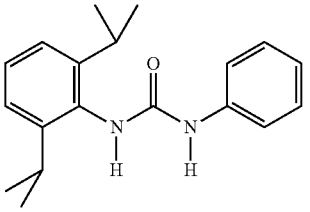 [SMILES: CC(C)c1cccc(C(C)C)c1NC(=O)Nc1ccccc1] | PhSiH₃ (1 eq.) | Fe(acac)₂ (5.0 mol %) + PP₃ (5.0 mol %) | THF | 100° C. | 63% |
| 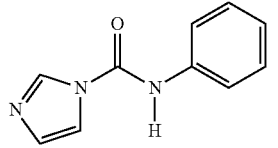 [SMILES: O=C(Nc1ccccc1)n1ccnc1] | PhSiH₃ (1 eq.) | Fe(acac)₂ (5.0 mol %) + PP₃ (5.0 mol %) | THF | 100° C. | 40% |

TABLE 1-continued

| Urea of formula (II) | Silane of formula (III) | Catalyst | Solvent | T (° C.) | Yield % |
|---|---|---|---|---|---|
| (dimethylamino-N'-phenyl urea) | PhSiH$_3$ (1 eq.) | Fe(BF$_4$)·6H$_2$O (5.0 mol %) + PP$_3$ (10.0 mol %) | THF | 100° C. | 35% |
| (imidazole-N-carboxamide, N-phenyl) | PhSiH$_3$ (2 eq.) | RuCl$_2$(DMSO)$_4$ (5.0 mol %) | THF | 100° C. | 45% |
| (N,N-diethyl-N'-phenyl urea) | PhSiH$_3$ (2 eq.) | RuCl$_2$(DMSO)$_4$ (5.0 mol %) | THF | 100° C. | 62% |
| (N,N-diethyl-N'-phenyl urea) | PhSiH$_3$ (2 eq.) | RuCl$_2$(DMSO)$_4$ (5.0 mol %) + dppb (5.0 mol %) | THF | 100° C. | 68% |
| (N,N-diethyl-N'-phenyl urea) | PhSiH$_3$ (2 eq.) | RuCl$_2$(DMSO)$_4$ (5.0 mol %) + PP$_3$ (5.0 mol %) | THF | 100° C. | 65% |
| (N,N-diethyl-N'-phenyl urea) | (CH$_3$)$_2$SiHO-SiH(CH$_3$)$_2$ (6 eq.) | RuCl$_2$(DMSO)$_4$ (10.0 mol %) | THF | 100° C. | 31% |
| (N-methyl-N,N'-diphenyl urea) | PhSiH$_3$ (2 eq.) | RuCl$_2$(DMSO)$_4$ (5.0 mol %) | THF | 100° C. | 51% |

The invention claimed is:

1. A process for the preparation of formamidines of formula (I):

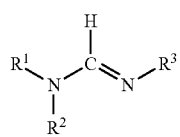

in which:

R$^1$ and R$^2$ represent, independently of one another, a hydrogen atom, an alkyl or aryl group, said alkyl and aryl groups being substituted optionally, or R$^1$ and R$^2$, taken together with the nitrogen atom to which they are bonded, form an optionally substituted heterocycle, and R$^3$ represents an alkyl group or an aryl group, said alkyl and aryl groups being optionally substituted, wherein a urea of formula (II), in which R$^1$, R$^2$ and R$^3$ are as defined above:

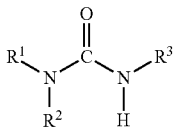

is reacted, in the presence of a catalyst, with a silane compound of formula (III):

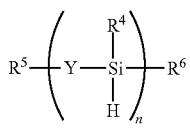

in which n is an integer varying from 1 to 20 000, and
when n=1, Y represents a single bond, and
$R^4$, $R^5$ and $R^6$ represent, independently of one another, a hydrogen atom, an alkyl, aryl alkoxy, silyl or siloxy group, or
when n>1, Y is an oxygen atom, and
$R^4$ represents an alkyl group,
$R^5$ represents a silyl group of formula —Si(X)$_3$ in which each X group, independently of one another, is chosen from an alkyl group,
$R^6$ represents a siloxy group of formula —O—Si(X)$_3$ in which each X group, independently of one another, is chosen from an alkyl group.

2. The process as claimed in claim 1, wherein the urea of formula (II),
$R^1$ and $R^2$ represent, independently of one another, a hydrogen atom, a linear or branched $C_1$-$C_7$ alkyl group, an aryl group chosen from phenyl or benzyl, said alkyl or aryl groups being optionally substituted, and
$R^3$ represents a linear or branched $C_1$-$C_7$ alkyl group, or an aryl group chosen from phenyl or benzyl, said alkyl and aryl groups being optionally substituted.

3. The process as claimed in claim 1, wherein the silane compound of formula (III):
n=1 and Y represents a single bond, and
$R^4$, $R^5$ and $R^6$ represent, independently of one another, a hydrogen atom, an alkyl, aryl, alkoxy, silyl or siloxy group.

4. The process as claimed in claim 3, wherein the silane compound of formula (III), $R^4$, $R^5$ and $R^6$ represent, independently of one another:
a hydrogen atom,
a linear or branched $C_1$-$C_7$ alkyl group,
an aryl group chosen from phenyl or benzyl,
a linear or branched $C_1$-$C_7$ alkoxy group,
a silyl group of formula —Si(X)$_3$ in which each X group, independently of one another, is chosen from a hydrogen atom an alkyl or alkoxy group,
a siloxy group of formula —O—Si(X)$_3$ in which each X group, independently of one another, is chosen from a hydrogen atom an alkyl or alkoxy group.

5. The process as claimed in claim 1, wherein the silane compound of formula (III):
n>1 and Y is an oxygen atom, and
$R^4$ is a methyl group,
$R^5$ represents a silyl group of formula —Si(X)$_3$ in which each X group, independently of one another, is chosen from a hydrogen atom or an alkyl group, $R^6$ represents a siloxy group of formula —O—Si(X)$_3$ in which each X group, independently of one another, is chosen from a hydrogen atom or an alkyl group.

6. The process as claimed in claim 5, wherein the silane compound of formula (III), n varies from 1000 to 5000.

7. The process as claimed in claim 1, wherein the catalyst is chosen from organic catalysts or metal catalysts, the metal catalysts being chosen from metal salts or metal complexes.

8. The process as claimed in claim 7, wherein the organic catalyst is:
a secondary or tertiary amine chosen from triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt or N-diisopropylethylamine (DIPEA or DIEA);
an alkyl- or arylphosphine chosen from triphenylphosphine, 2,2'-bis(diphenylphosphino)-1,1'-binaphthyl (BINAP) or triisopropylphosphine; an alkyl- or arylphosphonate chosen from diphenyl phosphate, triphenyl phosphate (TPP), tri(isopropylphenyl) phosphate (TIPP), cresyl diphenyl phosphate (CDP) or tricresyl phosphate (TCP); or an alkyl or aryl phosphate chosen from di(n-butyl) phosphate (DBP), tris(2-ethylhexyl) phosphate or triethyl phosphate;
an N-heterocyclic carbene, such as a carbene resulting from an imidazolium salt chosen from 1,3-bis(2,6-diisopropylphenyl)-1H-imidazol-3-ium, 1,3-bis(2,6-diisopropylphenyl)-4,5-dihydro-1H-imidazol-3-ium, 1,3-bis(2,4,6-trimethylphenyl)-1H-imidazol-3-ium, 1,3-bis(2,4,6-trimethylphenyl)-4,5-dihydro-1H-imidazol-3-ium, 4,5-dichloro-1,3-bis(2,6-diisopropylphenyl)-1H-imidazol-3-ium, 1,3-di(tert-butyl)-1H-imidazol-3-ium or 1,3-di(tert-butyl)-4,5-dihydro-1H-imidazol-3-ium salts, said salts being in the form of chloride salts, or
an oxygen-based base chosen from hydrogen peroxide, benzoyl peroxide or an alkoxide chosen from sodium or potassium methoxide, ethoxide, propoxide, butoxide, pentoxide or hexoxide.

9. The process as claimed in claim 8, wherein the organic catalyst is chosen from triazabicyclodecene (TBD), N-methyltriazabicyclodecene (MeTBD) or 1,8-diazabicyclo[5.4.0]undec-7-ene (DBU).

10. The process as claimed in claim 7, wherein the metal catalyst is chosen from the salts or complexes of:
metals chosen from boron, silicon, aluminum, gallium, tin or indium;
alkali metals chosen from sodium or potassium;
alkaline earth metals chosen from magnesium or calcium;
transition metals chosen from nickel, iron, cobalt, zinc, copper, rhodium, ruthenium, platinum, palladium or iridium; or
rare earth metals chosen from lanthanum, cerium, praseodymium or neodymium.

11. The process as claimed in claim 10, wherein the metal catalyst is a salt or complex of a transition metal chosen from nickel, iron, cobalt, zinc, copper, rhodium, ruthenium, platinum, palladium or iridium.

12. The process as claimed in claim 11, wherein the metal catalyst is:
a mixture of an Fe(acac)$_3$, Fe(acac)$_2$ or Fe(BF$_4$)$_2$.6H$_2$O iron salt with a ligand of phosphine or amine type chosen from TMEDA, dppe or PP$_3$; or
a mixture of a Cu(OAc)$_2$.H$_2$O or Cu(acac)$_2$ copper salt with a ligand of phosphine or amine type chosen from TMEDA, dppe or dpp; or a Zn(Et)$_2$ zinc salt; or a mixture of an RuCl$_2$(DMSO)$_4$ ruthenium salt with a ligand of phosphine type chosen from PP$_3$ or dpp.

13. The process as claimed in claim 1, wherein the reaction is at a temperature of between 50 and 150° C.

14. The process as claimed in claim 1, wherein the reaction is carried out for a period of time of 1 to 72 hours.

15. The process as claimed in claim 1, wherein the molar ratio of the urea of formula (II) to the silane compound of formula (III) is from 0.5 to 5.

16. The process as claimed in claim 1, wherein the amount of catalyst is from 0.001 to 1 molar equivalent with respect to the urea of formula (II).

17. The process as claimed in claim 1, wherein the reaction is at a temperature of between 75 and 125° C.

18. The process as claimed in claim 1, wherein the reaction is carried out for a period of time of 1 to 48 hours.

19. The process as claimed in claim 1, wherein the molar ratio of the urea of formula (II) to the silane compound of formula (III) is from 1 to 3.

* * * * *